United States Patent
Isobe et al.

(10) Patent No.: US 8,993,241 B2
(45) Date of Patent: Mar. 31, 2015

(54) REACTION DEVICE, REACTION METHOD AND METHOD OF SYNTHESIZING CDNA

(75) Inventors: Masaharu Isobe, Toyama (JP);
Nobuyuki Kurosawa, Toyama (JP)

(73) Assignee: National University Corporation University of Toyama, Toyama (JP)

( * ) Notice: Subject to any disclaimer, the term of this patent is extended or adjusted under 35 U.S.C. 154(b) by 473 days.

(21) Appl. No.: 12/863,185

(22) PCT Filed: Jan. 16, 2009

(86) PCT No.: PCT/JP2009/050585
§ 371 (c)(1),
(2), (4) Date: Oct. 7, 2010

(87) PCT Pub. No.: WO2009/091048
PCT Pub. Date: Jul. 23, 2009

(65) Prior Publication Data
US 2011/0020879 A1 Jan. 27, 2011

(30) Foreign Application Priority Data

Jan. 18, 2008 (JP) .................... 2008-008767

(51) Int. Cl.
| | |
|---|---|
| C12Q 1/68 | (2006.01) |
| C12M 1/34 | (2006.01) |
| C12M 3/00 | (2006.01) |
| B08B 3/04 | (2006.01) |

(Continued)

(52) U.S. Cl.
CPC .............. B08B 3/04 (2013.01); G01N 35/0098 (2013.01)
USPC ............. 435/6.12; 435/287.1; 435/287.2; 435/287.3; 435/288.2; 435/288.3

(58) Field of Classification Search
None
See application file for complete search history.

(56) References Cited

U.S. PATENT DOCUMENTS

| | | |
|---|---|---|
| 2005/0123954 A1 | 6/2005 | Feldsine |
| 2006/0182655 A1 | 8/2006 | Zou et al. |

(Continued)

FOREIGN PATENT DOCUMENTS

| | | |
|---|---|---|
| CN | 1434296 | 8/2003 |
| JP | 04-110579 | 4/1992 |

(Continued)

OTHER PUBLICATIONS

Radleys Discover Technologies PTFE microplates (Press Release Oct. 19, 2005).*

(Continued)

Primary Examiner — Teresa E Strzelecka
(74) Attorney, Agent, or Firm — Ditthavong & Steiner, PC (57) ABSTRACT

Provided is a device and a method whereby plural kinds of reaction operations and washing operations can be conducted in parallel without washing or replacing an instrument used in transferring a solution in each operation. A reaction device having a plurality of projecting barriers provided in a line on one surface of a substrate. The projecting barrier has a cutoff portion and an inner space capable of holding a droplet and having a contact angle to pure water of from 90 to 150 degrees. A reaction method using the reaction device wherein a substance immobilized on magnetic beads is sequentially transferred in and between droplets of a solution containing a surface tension reducing agent that are held in the spaces for holding a droplet by means of a magnet located on the opposite surface of the substrate to thereby conduct reactions and washings.

15 Claims, 5 Drawing Sheets

(51) Int. Cl.
  *C07H 21/02* (2006.01)
  *C07H 21/04* (2006.01)
  *G01N 35/00* (2006.01)

(56) References Cited

U.S. PATENT DOCUMENTS

2007/0105210 A1    5/2007  Delattre et al.
2007/0264675 A1*  11/2007  Toner et al. .................. 435/7.23

FOREIGN PATENT DOCUMENTS

| JP | 2003-315346 | 11/2003 |
| JP | 2006-105705 | 4/2006 |
| JP | 2006-349557 | 12/2006 |
| JP | 2007-504835 | 3/2007 |
| JP | 2007-512507 | 5/2007 |
| WO | WO 2007/102785 | * 9/2007 |

OTHER PUBLICATIONS

Yasuda, T. et al., Langmuir, vol. 10, pp. 2435-2439 (1994).*
ANSI/SBS Apr. 2004 Standard for microplates (Jan. 2006).*
Mata, A. et al., Biomed. Microdev., vol. 7, pp. 281-293 (2005).*
Thibault, C. et al., J. Nanobiotechnol., vol. 3, No. 7, pp. 1-12 (2005).*
Rangel-Lopez, A. et al., BMC Biotechnol., vol. 5:8, pp. 1-13 (2005).*
Chinese Office Action for corresponding CN Application No. 200980102879.8, Sep. 21, 2011.
Extended European Search Report for corresponding EP Application No. 09703047.2-2307, Apr. 19, 2012.
Pipper et al. Catching bird flu in a droplet, Nature Medicine, Oct. 2007, pp. 1259-1263, vol. 13, No. 10.
International Search Report for International Application No. PCT/JP2009/050585, Mar. 17, 2009.
Written Opinion of the International Searching Authority for International Application No. PCT/JP2009/050585, Mar. 17, 2009.
Supplementary Information (supplementary Figures 1-5) for Juergen Pipper et al., "Catching bird flu in a droplet", Nature Medicine, vol. 13, No. 10, Oct. 2007, pp. 1259-1263, Technical Reports.
Chinese Office Action for corresponding CN Application No. 200980102879.8, Aug. 9, 2012.
Japanese Notice of Allowance for corresponding JP Application No. 2009-550069, Mar. 26, 2013.
Chinese Office Action for corresponding CN Application No. 200980102879.8, Apr. 9, 2013.
Qian Zhimian, "Application Manual of Plastic Performance", Dec. 31, 1987, pp. 284-286.
Office Action for corresponding Canadian Application No. 2,712,572, dated Sep. 16, 2014, 2 pages.
Office Action for corresponding Korean Application No. 10-2010-7017949, dated Aug. 28, 2014, 5 pages (English Language Summary Included).

* cited by examiner

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial sequence
<220> FEATURE:
<223> OTHER INFORMATION: Synthetic primer

<400> SEQUENCE: 1
gaggacggct tgacaaacat gggg                                          24

<210> SEQ ID NO 2
<211> LENGTH: 24
```

-continued

```
<212> TYPE: DNA
<213> ORGANISM: Artificial sequence
<220> FEATURE:
<223> OTHER INFORMATION: Synthetic primer

<400> SEQUENCE: 2
acagaagtct gagaaggtca gggc                                              24
```

REACTION DEVICE, REACTION METHOD AND METHOD OF SYNTHESIZING CDNA

FIELD OF THE INVENTION

The present invention relates to a reaction device and a reaction method, particularly a reaction device and a reaction method capable of conducting a plurality of consecutive reactions optionally including a washing step, paratactically and conveniently. The present invention further relates to a method of synthesizing cDNA by using the device.

BACKGROUND ART

Generally, reactions relating genes including synthesis of cDNA from mRNA, amplification of DNA and the like are often conducted with a small volume and plural kinds of paratactic reactions. In such cases, in general, for example, a ninety-six well array, a three hundred and eighty-four well array or another micro well array is used, an array in which each well contains a reaction solution or a washing solution is prepared, and after completing reaction or washing operation the solution is transferred to the next well by means of a pipette, thereby the solution is subject to the next treatment. There is a situation that a robot is used to perform those treatments and operations conducted in routine.

However, even when a robot is used, a pipette which had been used for transferring a solution needs to be washed or replaced every time for using in next operation, and such operations are very troublesome.

It has been reported that instead of a pipette magnetic beads are employed and a sample immobilized on the magnetic beads is picked up and transferred by means of a magnet (for, example, JP Tokuhyo 2007-504835, Patent Document 1). However, when the micro well array mentioned above is used, a magnet for transferring is moved closer to the well from upside and in some case it needs to be immersed into a solution in the well. The magnet immersed into the solution needs to be washed before the next step. Also, the magnet needs to be demagnetizable in order to release the magnetic beads after the magnet is moved to the next step.

The non-patent publication 1 describes a RT-PCR reaction method using magnetic beads. In the method of the publication, a reaction at room temperature is carried out with adding 1 part of oil to 100 parts of a reaction solution, thereby the solution is covered with an oil membrane to avoid evaporation and the like.

Patent Document 1: Japanese Laid open patent publication Tokuhyou 2007-504835

Non-patent publication 1: Juergen Pipper, Masafumi Inoue, Lisa F-P Ng, Pavel Neuzil, Yi Zhang & Lukas Novak, NATURE MEDICINE VOLUME 13 NUMBER 10 October 2007 pp 1259-1263

SUMMARY OF INVENTION

Technical Problem

As described above, when a micro well array such as ninety-six well and three hundred and eighty-four well is used to conduct plural kinds of reaction operations and washing operations in parallel, even if a pipette or magnetic beads is used, the pipette or the magnetic beads needs to be washed or replaces for using in operations, so that the operations are troublesome.

Also, in the method of non-patent publication 1, a droplet is covered with oil membrane so as to avoid evaporation and the like, which makes its operation be troublesome. When a plurality of droplets is used, such troublesome operations are non-negligible.

An object of the present invention is to provide a device and a method for conducting plural kinds of reaction operations and washing operations in parallel without washing or replacing an instrument to be used for transferring a solution and the like every operation. A further object of the present invention is to provide a device or a method for conducting plural kinds of reaction operations and washing operations in parallel without covering a droplet with oil membrane.

Solution to Problem

The present invention is exemplified as follows:
(1) A reaction device characterized in that,
a plurality of projecting barriers are arranged in a line on either surface of a substrate, and the projecting barriers have at least one cutout portion and a space which can hold a droplet therein, and
at least the surface of the substrate holding the droplet has pure water contact angle of 90 to 150 degree.
(2) The reaction device described in (1), in which at least a part of or all of the plurality of projecting barriers are arranged in a matrix in a plane.
(3) The reaction device described in (1) or (2), in which spaces for holding a droplet of the projecting barriers can hold droplets of 0.5 μl~200 μl.
(4) The reaction device described in any one of (1) to (3), in which the projecting barriers have two or three cutout portions and the distance between the openings of the cutout portions is 0.5~10 mm.
(5) The reaction device described in any one of (1) to (4), in which the surface of the substrate consists of a paraffin resin, a teflon resin or a silicone resin.
(6) The reaction device described in any one of (1) to (4), in which the substrate comprises a coating layer made of a resin selected from the group consisting of a paraffin resin, a teflon resin and a silicone resin.
(7) The reaction device described in any one of (1) to (6), in which each space for holding a droplet defined by each projecting barrier holds a droplet of an identical or different solution so that a droplet does not contacted with another droplet held in a space for holding a droplet defined by another projecting barrier.
(8) The reaction device described in any one of (1) to (7), in which spaces for holding a droplet defined by projecting barriers residing in the same row crosswise hold droplets of the same kind of solution.
(9) The reaction device described in (7) or (8), in which the solution is a reaction solution or a washing solution, which solution contains a surface tension reducing agent.
(10) The reaction device described in any one of (1) to (9), which further comprises a housing member covering the surface having the projecting barriers and a moisturizing member providing humidity in the space covered by the housing member.
(11) A reaction method employing the reaction device described in any one of (1) to (10), in which method a substance immobilized on magnetic beads is sequentially transferred in or between droplets containing a surface tension reducing agent held in spaces for holding a droplet defined by projecting barriers by means of a magnet on the opposite surface of the substrate to the surface having the projecting barriers, so that a reaction and/or a washing is performed.
(12) A method of synthesizing cDNA employing the reaction device described in any one of (1) to (10) having at least two projecting barriers in one lengthwise row, which method comprises the steps of: that the spaces for holding a droplet defined by the two projecting barriers hold a droplet of cytolysis solution and a droplet of cDNA synthetic solution, which both solutions contain a surface tension reducing agent, in this sequence, respectively; that mRNA immobilized on magnetic beads is sequentially transferred into droplets held in the spaces for holding a droplet defined by the two projecting barriers by means of a magnet on the opposite surface of the substrate to the surface having the projecting barriers; and that cDNA immobilized on the magnetic beads is obtained.

(13) The method described in (12), in which method the reaction device having at least two projecting barriers in a plurality of longitudinal rows is used, the solutions held in the spaces for holding a droplet defined by projecting barriers in each crosswise row are the same solution, mRNA immobilized on the magnetic beads moving on the longitudinal rows are different each other, and plural different kinds of cDNA are obtained as cDNA immobilized on the magnetic beads.

(14) The method described in (12) or (13), in which method the reaction device has at least four projecting barriers in one longitudinal row, the spaces for holding a droplet defined by the four projecting barriers hold cytolysis solution, mRNA washing solution, cDNA synthetic solution and cDNA washing solution in this sequence, respectively, and mRNA immobilized on the magnetic beads is sequentially transferred into the solutions held in the spaces for holding a droplet defined by the four projecting barriers.

(15) The method described in any one of (11) to (14), in which method the reaction device is used in such a way that the surface having the projecting barriers is downward.

Effects of Invention

The present invention provides a device and a method for conducting plural kinds of reaction operations and/or washing operations in parallel without washing or replacing an instrument to be used for transferring a solution and the like per each operation of reaction, washing and etc.

BEST MODE OF CARRYING OUT THE INVENTION

[Reaction Device]

The present invention relates to a reaction device in which a plurality of projecting barriers are arranged in a line on one surface of a substrate and the projecting barriers have at least one cutout portion and a space for holding a droplet therein.

Figure 1:
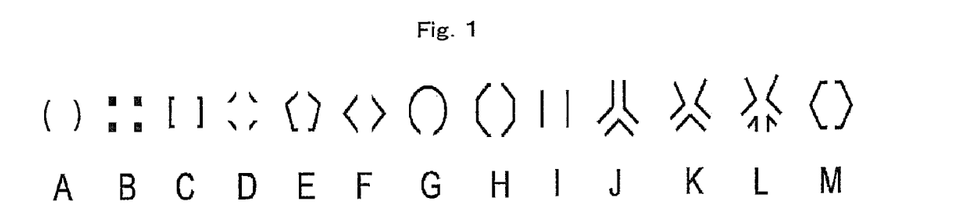
FIG. 1 shows examples of the shape of projecting barriers.

Any projecting barrier can be used as long as it has at least one cutout portion and a space for holding a droplet therein. A shape of a projecting barrier is any one selected from lots of shapes based on its intended use, particularly as exemplified by FIG. 1. For example, as shown in G of FIG. 1 the projecting barrier may be one having one cutout portion. A projecting barrier having one cutout portion is suitable for e.g. a reaction initiation position, a reaction termination position, or the final position. As shown in A, C, E, F, H, I and M of FIG. 1, a projecting barrier having two cutout portions is suitable for reaction operation or washing operation which is in the midstream of the entire process. A projecting barrier having three cutout portions as shown in J and K of FIG. 1, and one having four cutout portions as shown in B, D and L of FIG. 1 are suitable for using in the position where a sample reacted or washed is allotted for two or more. However, it is not limited to these usages.

Furthermore, projecting barriers arranged in one reaction device are not limited to one kind, and a plurality of projecting barriers having different shapes may appropriately be arranged.

The volume of a space for holding a droplet formed within a projecting barrier is arbitrarily chosen based on the application of the device or the function of the projecting barrier, but for example, it is within the range of 0.5 µl to 200 µl. However, it is not limited to the range, and the volume of a space for holding a droplet is arbitrarily decided based on the application.

With referring to an embodiment having U-shape projections as projecting barriers, the reaction device of the present invention is further explained based on FIG. 2 below. The U-shape projection, which is not shown in FIG. 1, has two cutout portions, and the openings formed by the cutout portions have different sizes each other. For example, the bigger opening can be used as an entrance, and the smaller one can be used as an exit.

Figure 2:
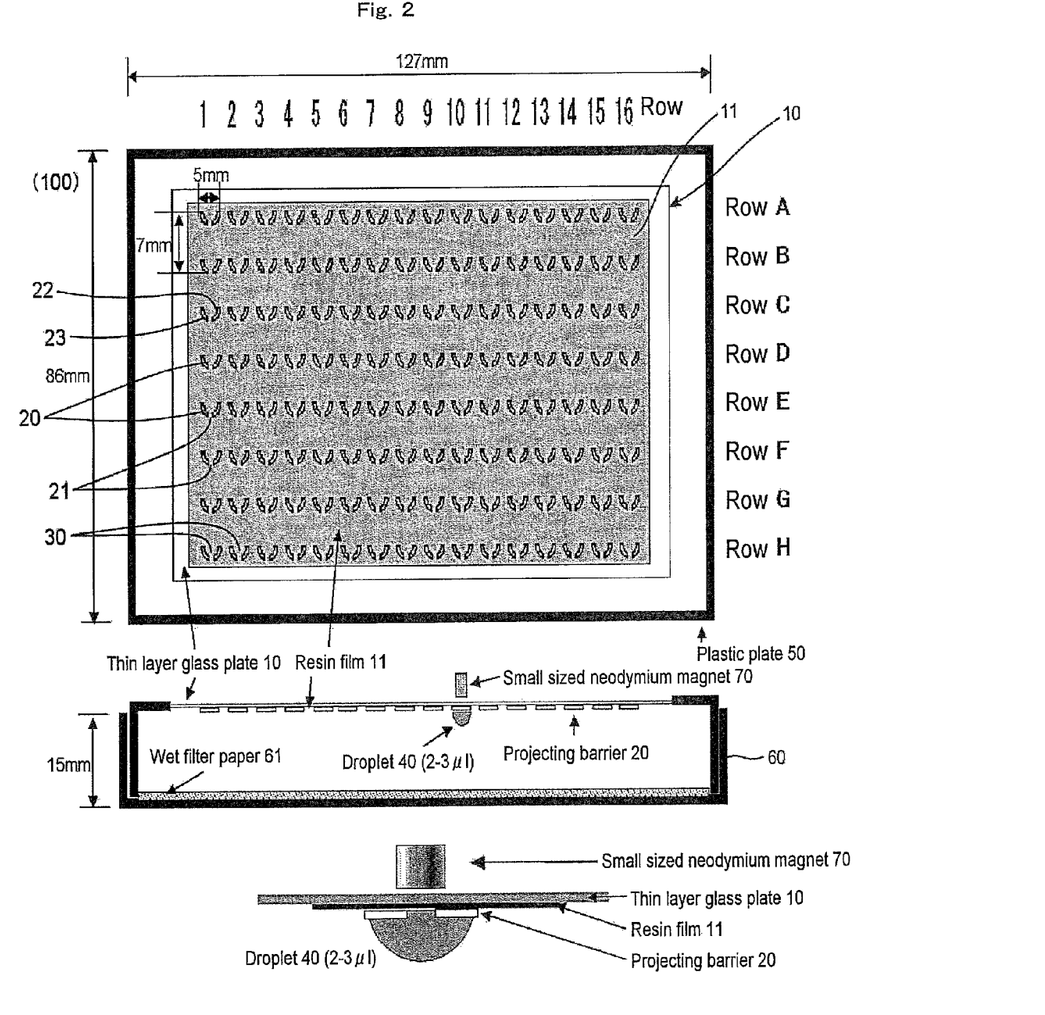
FIG. 2 is an explanation drawing showing one example of the reaction device of the present invention.

In the present invention, the reaction device 100, as shown in FIG. 2, has a plurality of U-shape projections 20 which are arranged on one side of the substrate 10 in a line with facing the same direction. The plurality of projections is arranged in a matrix in a place. The number of the U-shape projections forming lengthwise lines and the number of the U-shape projections forming crosswise lines are arbitrarily decided with considering the application of the reaction device, the number of reaction operations to be conducted at one time, and further, the size or shape of the substrate 10, the size or shape of the U-shape projections 20, the distance between the U-shape projections 20 each other, and the like. The number of the U-shape projections forming the lengthwise line, for example, is 2 to 10, and the number of the U-shape projections forming the crosswise line, for example, is 2 to 100, but it is not limited to such numbers. The reaction device shown in FIG. 2 has U-shape projections which are arranged in 16 rows crosswise and 8 rows lengthwise.

The U-shape projection, as shown in FIG. 2, consists of two projections 22 and 23 which are arranged via the gap 21 formed by the cutout. The U-shape projection has the space 30 capable of holding the droplet 40 therein, and the volume to be held in the space, for example, is in the range of 0.5 µl to 200 µl, but it is not limited to this range. The shape of the projections 22 and 23 is not limited as long as the space 30 can hold a droplet of the above volume. However, from the view point that the space 30 can hold a droplet within its space effectively, a partially circular shape or a partially elliptic shape is preferably employed, but it may be a shape formed by one straight line or a plurality of straight lines (e.g., V-shape). The height of the projection 22 and 23 is not limited as long as the space 30 can hold a droplet of the above volume. The height of the projection 22 and 23 is, for example, in the range of 1 to 5 mm.

The gap 21, as described later, is a transfer conduit where magnetic beads are transferred together with a reaction product immobilized thereto when the reaction product, which is immobilized on the magnetic beads after the completion of a treatment operation, is transferred from a droplet held in the space 30 within a U-shape projection to a droplet held in the space 30 within the next U-shape projection. Therefore, the shortest distance of the gap 21 is decided by the view point that the U-shape projection can act as a defense wall against transferring so that the magnetic beads can easily transfer into the space 30 of the next U-shape projection but the droplet held in the space 30 of the U-shape projection is prevented from transferring into the space 30 of the next U-shape projection with the magnetic beads. From such view point, the shortest distance of the gap 21, for example, is 1 to 10 mm.

On the other hand, the ends of the projections 22 and 23 positioned in the opposite side of the gap 21 is preferably opening from the view point that it makes the magnetic beads be easily transferred and forms a space for holding a droplet.

In the present invention, it is preferable that at least the droplet holding surface of a substrate of a reaction device is positioned at no vertical interval with the surfaces of another substrate and is flat from the view point of the simplicity of manufacturing substrates. However, in the present invention, at least the droplet holding surface of a substrate of a reaction device may be positioned below another substrate surface and can form craters thereon. The crater makes holding a droplet be easier than flat. However, it is appropriate that the depth of a crater or the shape of surface of the crater is insomuch as not interfering with the transfer of magnetic beads from the droplet held. It is appropriate that, within surfaces forming a crater, at least the surface which leads up to an opening of a projection and on which magnetic beads may move is a curved surface not having a bump. Further, it is appropriate that the depth of crater, for example, is less or equal to the half of an opening size of a projection, and the maximal slope of a surface forming a crater is or less than 45 degree.

In the present invention, it is appropriate that at least the droplet holding surface of a substrate has a contact angle with pure water of 90 to 150 degree from the view point of retention of a droplet in a space and prevention of contact between droplets held in each space. Even though a projecting barrier holds a droplet therein, there may be a case that the droplet cannot appropriately be held only by the projecting barrier during reaction operations using magnetic beads described later. Thus, in the present invention, at least an internal surface of a projecting barrier has a contact angle with pure water of 90 to 150 degree in order to appropriately hold a droplet within the projecting barrier. The contact angle with pure water may change based on a material forming a surface and a condition of surface such as its roughness or shape and the like. Even when the material is the same, if the surface condition such as surface roughness or shape is different the contact angel with pure water changes. In the present invention, a material forming a surface and a surface condition such as surface roughness or shape and the like is selected so that its contact angle with pure water becomes within the range of 90 to 150 degree.

As a material forming a surface, a paraffin resin, a Teflon® resin or a silicone resin, which is relatively high water repellent material, may be used. A substrate may be made of these materials, or a substrate may be made of another material such as a glass plate and coated its surface with the above mentioned paraffin resin, Teflon® resin or silicone resin or the like. These materials have high water repellency by themselves, so that even a flat surface of these materials can have a contact angle within the range described above. However, if desired, a surface can be rough so as to control its contact angle.

For example, when a paraffin resin is used, in the reaction device shown in FIG. 2, small corrugated concavo-convex (surface roughness), which are oriented in parallel with the lengthwise direction of U shape of each U-shape projection, can be arranged on the surface of the substrate 10. The small corrugated concavo-convex makes the movement of magnetic beads be easy because of being oriented in parallel with the lengthwise direction of U shape of each U-shape projection.

Small corrugated concavo-convex is not limited as long as it has the function described above, but it, for example, is 1 μm to 1 mm in height and 1 μm to 1 mm in wave length. Further, a shape of concavo-convex is adjusted so that a surface having the small corrugated concavo-convex provides a contact angle with pure water of 90 to 150 degree.

In the space 30 of each U-shape projection 20, droplets of the same or different kind of solution are used to be held in such a way that it is not blended with another solution held in the space of another U-shape projection. A solution held in the space 30 as a droplet is not limited, but it, for example, is a reaction solution or a washing solution. The kind of a reaction solution or a washing solution is arbitrarily selected based on its application purpose of the reaction device of the present invention.

It is just as well that a surface tension reducing agent is added to a reaction solution or a washing solution to be used. A surface tension reducing agent has an effect of reducing surface tension of solution, thereby a droplet is stably held on a hydrophobic substrate. A surface tension reducing agent also has an effect of reducing surface tension of a droplet which would prevent the movement of a group of magnetic beads out of the droplet. In the present invention, as described above, at least a surface forming a space for holding a droplet has a contact angle with pure water of 90 to 150 degree and has relatively water repellent property, and a surface tension reducing agent is added to the droplet held therein, as a result, it prevents the spreading of the droplet out of the surface of the space for holding a droplet and gives the adherability of the droplet to the surface of the space for holding a droplet, and a holding force is increased, and thereby the holding of the droplet on the surface of the space for holding a droplet can be maintained when magnetic beads move into or out of the droplet. Also, the surface between a projecting barrier and the nearby projecting barrier may equally have a contact angel with pure water of 90 to 150 degree, but with considering the simplicity of movement of magnetic beads the surface between a projecting barrier and the nearby projecting barrier may have a different property.

Also, an addition of a surface tension reducing agent provides an advantage that magnetic beads can easily move into or out of a droplet particularly when magnetic beads having relatively small particle size are used.

As a surface tension reducing agent, it is suitable an agent which for example can reduce a contact angel with pure water on a glass plate (in Table 1 described later, the measurement result is 42 degree) to 30 degree or less when its concentration of 0.1% in pure water. Examples of an agent having such surface retention reducing effect are a surfactant and a lipoprotein such as lung surfactant protein, a serum albumin or a serum containing lots of lipoproteins and the like.

There are many kinds of surfactants, and regardless of its kind, they are used as a surface tension reducing agent. Here lists, but they are mere exemplifications and it is not intended to limit to these.

(1) Anion surfactants: sodium fatty acid, monoalkyl sulfate
(2) Cation surfactants: Alkyl polyoxyethylene sulfate, alkyl benzensulfonate, monoalkyl phosphate
(3) Ampholytic surfactants: alkyl trimethyl ammonium salt, dialkyl dimethyl ammonium salt, alkyl benzyl dimethyl ammonium salt, alkyl dimethyl amine oxide, alkyl carboxy betaine
(4) Nonionic surfactants: polyoxyethylene alkylether, fatty acid sorbitan ester, alkylpolyglucoside, fatty acid diethanol amide, alkyl monoglyceryl ether Dodecyl lithium sulfate can be listed as a representative example of anion surfactant, and Triton X100 can be listed as a representative example of nonionic surfactant.

Additive amount of a surface tension reducing agent is, for example, 0.001 to 1%, preferably 0.01 to 1% with the consideration of the above points and considering the kind of a surface tension reducing agent and a contact angle with pure water of the surface of a space for holding a droplet, but it is not limited to these ranges.

In a reaction device of the present invention, when different kinds of samples are subject to the same reaction treatments or operations, spaces of U-shape projections belongs to the same row crosswise may hold droplets of the same kind of solution.

A reaction device of the present invention may further have a housing member covering a surface having projecting barriers and a moisture member supplying humidity in the space covered by the housing member. For example, as shown in FIG. 2, a thin-layer glass plate 10 is positioned on the bottom opening of a box plastic plate 50, on which plate a resin film 11 having projecting barriers is attached so that the projections face to the inside of the plastic case. Another housing member (cover) 60 may further be arranged to cover the upper opening of the plastic plate. A moisture member 61 such as a wet paper, which supplies humidity in the space covered by the housing member, may be arranged within the housing member (cover) 60. With having such conformations, when a small amount of droplet is operated, volatilization of water from the droplet is inhibited, and thereby reaction or washing operations and the like are carried out smoothly and acceptably. Magnetic beads are sequentially transferred by a magnet 70 such as a small-seized neodymium magnet on the opposite surface (the upper of FIG. 2) of the substrate 10 to the surface having projecting barriers 20, so that operations of reactions, washings and so on can be carried out.

[Reaction Method]

The present invention includes a reaction method using the reaction device of the present invention mentioned above. The reaction method of the present invention includes the steps of reaction and washing in which a substance immobilized on magnetic beads is sequentially transferred in or between droplets of solution including a surface tension reducing agent held in a space of a projecting barrier such as U-shape projections by means of a magnet on the opposite surface of the substrate to the surface having projecting barriers. The temperature of reaction and washing can be arbitrarily decided with considering a suitable temperature for reaction and washing, and temperature can be controlled to go up and down for each step. In such a case, if necessary, a heating and/or cooling equipment can be set up, for example, outside or within the housing members 50 and/or 60, and/or between the thin layer glass plate 10 and the resin film 11 or on the opposite surface of the substrate to the surface having the projecting barriers.

In a reaction method of the present invention, the reaction device is preferably used in a manner that the surface having projecting barriers looks downward. When the surface having projecting barriers is used to look downward, droplets held by the projecting barriers are in hanging drop condition. When the reaction method is conducted in such a way, since water is vaporized upward because of lightweight of vapor, vaporizing can be inhibited if droplets are in hanging drop condition. As a result, conducting the method even in an open system, vaporizing is considerably inhibited under room temperature. Furthermore, when the surface having projecting barriers of the reaction device is housed into a housing member or when the surface having projecting barriers of the reaction device is positioned in housing member where a moisture member is provided, water vaporizing from droplets can be further inhibited. By employing such a manner, water vaporizing from droplets can be inhibited without using oil as described in non-patent publication 1. If oil is not used, oil is not attached to a pipette even when a very small amount of reaction solution such as several micro liters is used. As a result, there is an advantage that addition or collection of solution can be easily conducted at any time. Under the condition of room temperature and no wind, even when a moisture member is not used and non-closed system is employed (that is, the device is not within a housing member (case)), hanging drops of several micro liter can maintain for several hours without drying. However, when the temperature for conducting an enzyme reaction is higher than room temperature, for example, the enzyme reaction is carried out at or around 50° C., vaporizing can not be disregard. In such a case, operations of reaction and etc. can preferably carried out within a case (housing member) in which a moisture member is.

When a surface having projecting barriers of a reaction device is housed in a housing member, it is preferable to heat up to, for example, 30 to 40° C. the interior portion formed by the reaction device and the housing member before and during operations of reaction and so on as long as such temperature does not have any effect on a reaction and so on. Water vapor, which is produced by heating, is precipitated and forms minuscule droplets, which minuscule droplets makes the movement of magnetic beads from a droplet become smoothly. Particularly, when a reagent having relative low surface tension reducing effect, concretely a reagent other than a surfactant, is used, there is an advantage that this heating makes the movement of magnetic beads become more smoothly. Also, from the view point of the acceleration of precipitation of water vapor on the surface of substrate, it can be to cool a reaction device covered by a housing member, for example, to conduct operations in a room at relatively low temperature.

Also, another advantage of making droplets be in hanging drop condition is that agitation of magnetic beads in the droplets is accelerated. When a magnet gets off a substrate, magnetic beads in droplets caught and held by the magnet fall down to the bottom of droplets which are in hanging drop condition by gravity, and the magnet attaches to the substrate again so that the magnetic beads aggregate on the surface of the substrate from the bottom of droplets. This operation can make efficiency of washing of magnetic beads, enzyme reaction and the like be increased. The catching and the falling of magnetic beads in droplets in hanging drop condition by a magnet may be conducted for one time or repeated for plural times.

Commercially available magnetic beads can be used as magnetic beads in the present invention. The particle size of magnetic beads is, for example, 0.01 µm to 2 mm, preferably 0.1 µm to 0.1 mm, but when the particle size of magnetic beads becomes small to nano-size, there may be the case that their moving into or out of droplets becomes difficult. In such case, magnetic beads having larger particle size can be used in combination as a carrier, which makes the moving into or out of droplets becomes easy. The beads to be used in combination as a carrier does not immobilize a substance, but carrier beads on which a substance is immobilized can be used in combination.

In addition, a substance as an object to be reacted or treated by the reaction method of the present invention is immobilized on the surface of magnetic beads. Immobilization of a substance can be carried out by a conventional method. The substance as an object to be reacted or treated is not particularly limited, but may be nucleic acid (DNA, RNA and so on), peptide, protein, sugar, lipid, complex glycolipid, natural low molecular, synthetic low molecular, high-molecular compound, metal and the like. The reaction method of the present invention can be applied to both large-scale or small volume sequentially reactions using nucleic acids, proteins, lipids, sugars, complex carbohydrates, or chemical compounds, and immunostaining of the immobilized cells (one to more than a dozen cells) can be used.

The amount of a substance to be immobilized as an object for a reaction treatment to magnetic beads is arbitrarily decided with considering the kind of a material, the kind of a reaction, etc.

As an example of the reaction method of the present invention, a synthesis method of cDNA is listed. The synthesis method of cDNA of the present invention uses a reaction device of the present invention, in which device at least two projecting barriers are arranged in one lengthwise row. The spaces for holding a droplet defined by the two projecting barriers hold a cytolysis solution containing a surface tension reducing agent and cDNA synthesis solution containing a surface tension reducing agent in this order, respectively, and an mRNA immobilized on magnetic beads is sequentially transferred into the solutions held in the spaces for holding a droplet defined by the two projecting barriers by means of a magnet on the opposite surface of the substrate to the surface having the projecting barriers, and thereby cDNA immobilized on the magnetic beads is obtained.

In the cDNA synthesis method of the present invention, as described above, the reaction device is preferably used in the condition that the surface having projecting barriers faces downward. When the device is used in the condition that the surface having projecting barriers faces downward, droplets held by projecting barriers take a hanging drop condition, and thereby the effects of agitation acceleration of magnetic beads and inhibition of water vaporization are obtained.

Figure 3:
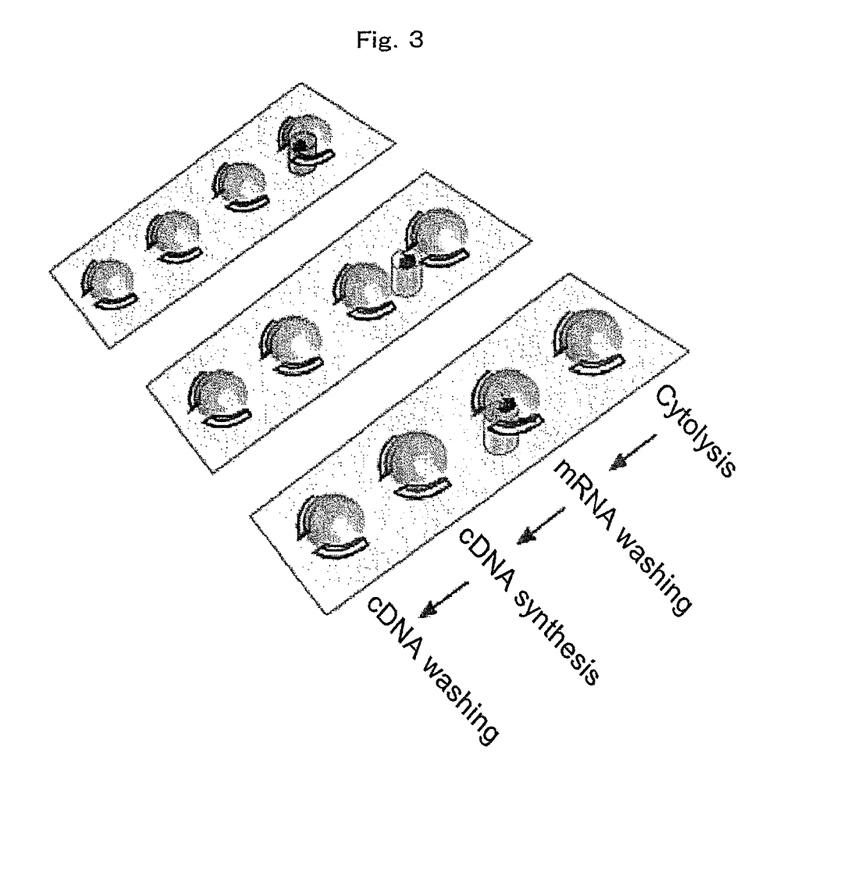
FIG. 3 is an explanation drawing showing cDNA synthesis method using the reaction device of the present invention.

The cDNA synthesis method of the present invention preferably employs a reaction device in which at least four projecting barriers are arranged in one lengthwise row. The spaces defined by the four projecting barriers such as U-shape projections hold a cytolysis solution, an mRNA washing solution, a cDNA synthesis solution and a cDNA washing solution in this order, respectively (referring to FIG. 3), and an mRNA immobilized on magnetic beads is sequentially transferred into droplets held in the spaces defined by the four projecting barriers by means of a magnet on the opposite surface of the substrate to the surface having the projecting barriers of the substrate, and thereby cDNA immobilized on the magnetic beads is obtained.

In the cDNA synthesis method of the present invention, the volume of a space defined by a U-shape projection of a reaction device is just as well, for example, in the range of 0.5 to 100 μl.

The cytolysis solution held in the space defined by the first U-shape projection is, for example, a solution of 3 μl in total, which contains 100 mM Tris HCl (pH 7.5), 500 mM LiCl, 1% dodecyl lithium sulfate and 5 mM dithiothreitol.

The mRNA washing solution held in the space defined by the second U-shape projection is, for example, a solution of 3 μl in total, which contains 10 mM Tris HCl (pH 7.5), 0.15M LiCl and 0.1% dodecyl lithium sulfate.

The reverse transcription reaction washing solution held in the space defined by the third U-shape projection is, for example, a solution of 3 μl in total, which contains 50 mM Tris HCl (pH8.3), 75 mM KCl, 3 mM $MgCl_2$, 0.1% Triton X-100, 0.5 mM dNTP, 5 mM DTT and 2 units RNase inhibitor.

The reverse transcription reaction solution held in the space defined by the fourth U-shape projection is, for example, a solution of 3 μl in total, which contains 50 mM Tris HCl (pH8.3), 75 mM KCl, 3 mM $MgCl_2$, 0.1% Triton X-100, 0.5 mM dNTP, 5 mM DTT, 2 units RNase inhibitor and 8 units SuperScript III Reverse transcriptase.

However, these are exemplifications, and it is not limited to these exemplified solutions.

An mRNA immobilized on magnetic beads is prepared. mRNA is not limited for its kind, length and so on. Any kind of mRNA of biological origin can be used. Magnetic beads, for example, which have the particle size of 2.8 μm and oligo dT25 covalently bound to the surface, are used. Immobilization of mRNA on magnet beads can be conducted by the followings.

Magnetic beads are suspended in a cytolysis solution with the concentration of 10 mg/ml. One to 100 cells are added to the solution. By these procedures, mRNA in cells is, via its polyA tail, bound to oligodT25 immobilized on magnet beads.

A mRNA immobilized on magnetic beads is sequentially transferred into the solutions (droplets) held in spaces defined by the four U-shape projections by means of a magnet on the opposite surface of a substrate to the surface having projections. The magnet is, for example, a small size neodymium magnet. The magnet beads are maintained in each droplet for required time for reaction or washing. The required time for reaction or washing depends on reaction condition and washing condition, but for example, is between 1 second to 1 hour.

The above reaction and washing can be carried out at normal temperature or room temperature, but if needed, temperature can be controlled. Further, when a droplet has a small amount, there may be a case that a solvent of a solution is vaporized, and thus, it is preferable that a reaction device is placed in a closed container and the humidity in the container keeps constant, thereby vaporization of solvent is avoided. In order to keep the humidity in the container be constant, a vessel containing water or other suitable aqueous solution can co-exist in the above closed container.

The mRNA immobilized on magnet beads sequentially abides in and passes through the solutions/droplets held by the spaces defined by the above four U-shape projections to obtain cDNA immobilized on the magnetic beads. The thus obtained cDNA can be subjected to the next step without be cut from the magnetic beads.

In the above cDNA synthesis method, a reaction device in which at least four U-shape projections are arranged in plural of rows lengthwise (for example, of 2 to 50 rows), is used, and the solutions held by the U-shape projections in each crosswise row are the same and mRNAs immobilized on magnetic beads which are transferred lengthwise row are different kinds of mRNA, and thereby plural different kinds of cDNA can be obtained as cDNA immobilized on magnetic beads.

Figure 4:
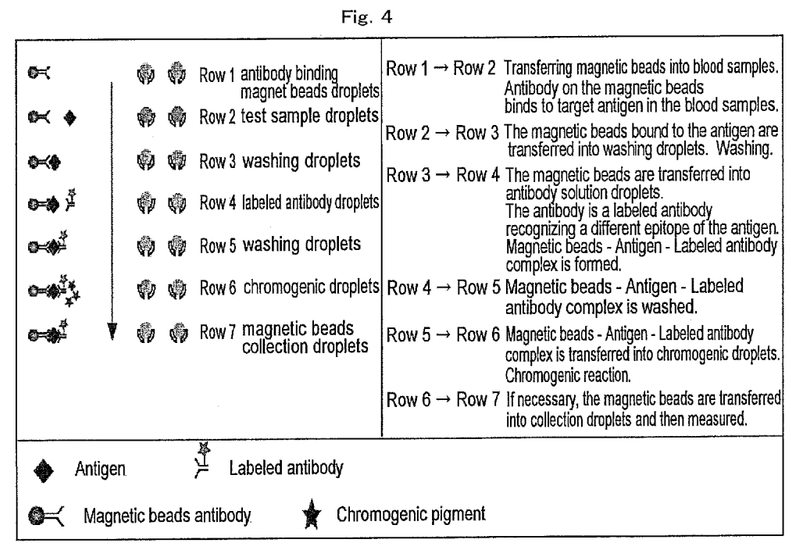
FIG. 4 shows a reaction example by means of antibody binding magnetic beads.

An example of reaction using antibody binding magnetic beads is shown in FIG. 4. FIG. 4 is a diagram of the reaction device looked from below, in which droplets are in hanging drop condition. This reaction uses antibody binding magnetic beads which specifically bind to a target antigen.

It spots an antibody magnetic beads (0.1% Triton X-100, 150 mM NaCl, 10 mM sodium-potassium phosphate buffer pH 7.0, 25 μg/3 μl antibody binding magnet beads having the particle size of 1.0 μm to 2.8 μm) in the first row, a sample to be tested in the second row, a washing solution (0.1% Triton X-100, 150 mM NaCl 10 mM sodium-potassium phosphate buffer pH 7.0) in the third row, a labeled antibody (which is specific to a target antigen, recognizes an epitope different from one recognized by the antibody immobilized on the magnetic beads, and has a labeling such as alkaline phosphatase labeling, peroxidase labeling, fluorescent dye labeling and gold particle labeling) in the fourth row, a washing solution in the fifth row, and a fluorescent solution in the sixth row. However, these compositions of each solution forming spots are examples, and it is not limited to these.

With using a small sized magnet, the antibody magnet beads in the droplet of the first row are transferred into the droplet of the sample to be tested in the second row, and antigen-antibody reaction is carried out, for example, for 10 to 60 min. at room temperature. During this period, the plate is turned over or the magnetic beads fallen down to the bottom of droplets are moved to the upper portion of the plate by using the magnet, and thereby the magnetic beads are agitated.

After the magnetic beads are transferred into the washing solution in the third row, the beads are agitated and washed for, e.g. 5 min.

After transferring the magnetic beads into the labeled antibody droplet in the fourth row, antigen-antibody reaction is carried out, for example, for 10 to 60 min. at room temperature. During this period, the plate is turned over or the magnetic beads fallen down to the bottom of droplets are moved to the upper portion of the plate by using the magnet, and thereby the magnetic beads are agitated.

After the magnetic beads are transferred into the washing solution in the fifth row, the beads are agitated and washed for, e.g. 5 min.

After transferring the magnetic beads into the fluorescent solution in the sixth row, emission or chemiluminescence reaction is carried out according to a label compound. In a case that magnetic beads prevent the detection or that the reaction needs to be stopped, the magnetic beads are transferred into the seventh row, and thereby the emission or chemiluminescence of droplets in the sixth row can be measured.

As described above, the reaction can be carried out by using antibody binding magnetic beads.

Figure 5:
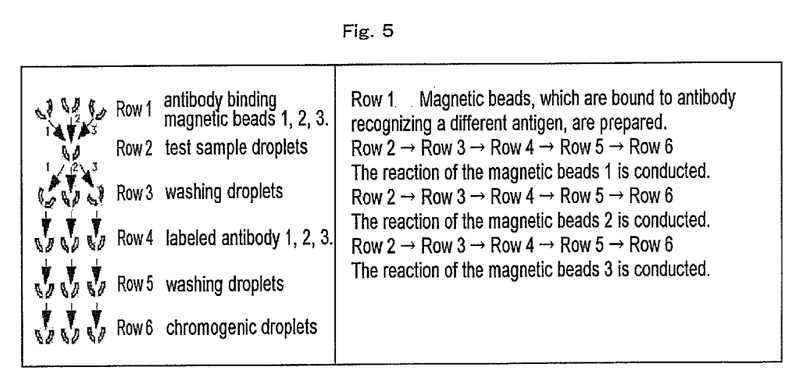
FIG. 5 shows an example of the method of detecting a plurality of antigens with one sample.

FIG. 5 shows an example of a reaction method in which plural number of antigens can be detected with one sample. Here, it exemplifies that three kinds of antigens can be detected simultaneously from one sample to be tested.

Antibody magnetic beads specific to antigens A, B and C are spotted in the droplet holding projections 1, 2 and 3 in the first row, respectively.

It spots a test sample in the second row, a washing solution (0.1% Triton X-100, 150 mM NaCl 10 mM sodium-potassium phosphate buffer pH 7.0) in the third row, a labeled antibody (which is specific to a target antigen, recognizes an epitope different from one recognized by the antibody immobilized on the magnetic beads, and has a labeling such as alkaline phosphatase labeling, peroxidase labeling, fluorescent dye labeling and gold particle labeling) in the fourth row, a washing solution in the fifth row, and a fluorescent solution in the sixth row. However, these compositions of each solution forming spots are examples, and it is not limited to these.

The antibody magnetic beads in the droplet holding projection 1 in the first row are transferred into the droplet of the test sample in the second row. After a reaction is carried out, for example, for 10 to 60 min. at room temperature so that antigen A binds to the magnetic beads 1, the magnetic beads are transferred into the washing droplet 1 in the third row.

The antibody magnetic beads in the droplet holding projections 2 in the first row are transferred into the droplet of the test sample in the second row. After a reaction is carried out, for example, for 10 to 60 min. at room temperature so that antigen B binds to the magnetic beads 2, the magnetic beads are transferred into the washing droplet 2 in the third row.

The antibody magnetic beads in the droplet holding projections 3 in the first row are transferred into the droplet of the test sample in the second row. After a reaction is carried out, for example, for 10 to 60 min. at room temperature so that antigen C binds to the magnetic beads 3, the magnetic beads are transferred into the washing droplet 3 in the third row.

After the magnetic beads 1, 2 and 3 are transferred into the labeled antibody droplet 1, 2 and 3 in the fourth row, respectively, a antigen-antibody reaction is carried out, for example, for 10 to 60 min. at room temperature.

The magnetic beads 1, 2 and 3 are transferred into the washing droplets 1, 2 and 3 of the fifth row, respectively.

The magnetic beads 1, 2 and 3 are transferred into the fluorescent solutions 1, 2 and 3 in the sixth row, and then emission or chemiluminescence reaction is carried out for a certain period of time, so that the thus obtained emission or luminescence is detected by using a detector.

As described above, the reaction for detecting plural of antigens can be conducted.

EXAMPLES

Here, the present invention is further explained by referring examples.

As shown in FIG. 2, the bottom of a plastic plate 50 (127 mm×86 mm×15 mm) is cut off, and a thin layer glass plate 10 (0.15 mm of the thickness) or a plastic plate (0.15 mm of the thickness) is inlaid therein. Since the magnetic force of a small size neodymium magnet is not sufficient, the bottom face is replaced with a thin plate.

A paraffin resin film 11 (trade name: PARAFILM) was pressure bound on the above thin layer glass plate. On the paraffin resin film there are tiny grooves in a direction orthogonal to the expansion direction of the film, which grooves is useful for guiding the transfer of magnetic beads. The paraffin resin film makes tulip-shaped projections and the like be easily formed.

On the above paraffin resin film, tulip-shaped projections were prepared with necessary numbers by a jig in advance. The projections formed on the paraffin resin film are the U-shape projections for stably holding solutions on the film, which solutions are used for magnetic beads washing, enzyme reaction and so on. It refers to FIG. 2. There are 1 to 16 rows and A to H rows of tulip-shaped projections. The contact angle with pure water of paraffin resin film was 112 degree.

The contact angles with pure water and with 0.1% Triton X-100 aqueous solution of paraffin resin, teflon resin, silicone resin, galas plate, acrylic plate and copper plate are shown in Table 1 below.

The measurements were carried out by the followings. Three µl of pure water were allowed to stand on the surface of each material, and then after five minutes, the conditions of droplets were observed with a microscope. The height of the droplet A and the length of the side B, which contacted with the surface of a material, were measured to calculate contact angle with water θ by using the calculating formula below.

Formula 1:

$\theta = 2 \tan^{-1} 2A/B$

TABLE 1

|  | Contact angle with pure water | Contact Angle with 0.1% Triton X-100 aqueous solution |
| --- | --- | --- |
| Paraffin resin | 112 | 55 |
| Teflon resin | 102 | 40 |
| Silicone resin | 100 | 59 |
| Glass plate | 42 | ND |
| Acrylic plate | 84 | ND |
| Copper plate | 81 | ND |

ND: Incapable of measurement because the droplet was spread on the surface.

A cylindrical neodymium magnet having 1.5 mm of the diameter and 2 mm of the height was used for transferring magnetic beads.

Example 1

Preparation of cDNA for 5'-RACE cDNA for 5'-RACE was prepared according to the protocols described below.
[Dispensing of Solution]
To 3 μl of a cytolysis solution containing mRNA binding magnetic beads (25 μg), 1 to 100 cells of B lymphocyte cell are added and dissolves so that mRNA eluted from the cells were captured on the mRNA binding magnetic beads.

Two to three μl of the above solution was spotted on the center of tulip-shaped projections in the row A—Cytolysis solution droplet.

Two to three μl of mRNA washing solution was spotted on the center of tulip-shaped projections in the row B—Cell washing solution droplet.

Two to three μl of reverse transcription reaction washing solution was spotted on the center of tulip-shaped projections in the row C—reverse transcription reaction washing solution droplet.

Two to three μl of reverse transcription reaction solution was spotted on the center of tulip-shaped projections in the row D—reverse transcription reaction solution droplet.

Two to three μl of 3'-tailing reaction washing solution was spotted on the center of tulip-shaped projections in the row E—3'-tailing reaction washing solution droplet.

Two to three is μl of 3'-tailing reaction solution was spotted on the center of tulip-shaped projections in the row F—3'-tailing reaction solution droplet.

Two to three μl of reaction stopping solution was spotted on the center of tulip-shaped projections in the row G.

Two to three μl of PCR reaction solution was spotted on the center of tulip-shaped projections in the row H.

A cover was put on the plate and they were turned over so that the solution was held in hanging drop condition on the film (for the purpose of the inhibition of vaporization and the agitation of magnetic beads owing to gravity). A filter paper containing water was pressure bound to the inside of the cover (for the purpose of the inhibition of vaporization).
[Transferring from Row A to Row B]

A small sized neodymium magnet was placed on the thin layer glass plate in the bottom of the plate so that the magnet was faced to the center of the cytolysis solution droplet in the row A, and then stood stationarily for 1 second.

The small sized neodymium magnet was transferred to the direction from the cytolysis solution droplet in the row A to the mRNA washing solution droplet in the row B, at a slow speed with taking about 2 seconds. On this occasion, the group of magnetic beads bound to mRNA was, as a droplet of several dozens of nanoliters, left from the cytolysis solution droplet in the row A and transferred into the mRNA washing solution droplet in the row B.

The small sized neodymium magnet was taken off the glass plate. The magnetic beads gathered on the resin film by magnetic force were fallen toward the bottom of the mRNA washing solution droplet by gravity. On this occasion, solution attached on the periphery of magnetic beads was washed out. If necessary, the plate is tilted back and forth and around to agitate magnetic beads in the droplet so that washing effect is increased.
[Transferring from Row B to Row C]

After the magnetic beads were fallen on the bottom of the droplet, in a similar way with the above described operations, the small sized neodymium magnet was placed toward the center of mRNA washing solution droplet in the row B, and then stood stationarily for 1 second. Then, the magnet was moved to the reverse transcription reaction washing solution droplet in the row C.
[Transferring from Row C to Row D]
Reverse Transcription Reaction After the magnetic beads were transferred into the reverse transcription reaction solution droplet in the row D, the plate kept in an inverted condition and maintained in a warmer of 37 to 50° C. for 1 hour. During this period, every ten minutes, the plate was tilted back and forth and around to agitate magnetic beads in the droplet so that enzyme reaction was carried out sufficiently.
[Transferring from Row D to Row E]
Magnetic beads were washed out.
[Transferring from Row E to Row F]
3'-Tailing Reaction The plate was inverted and kept at 37° C. for 1 hour. In a similar manner of the reverse transcription reaction, agitation of magnetic beads was carried out.
[Transferring from Row F to Row G, Followed by Transferring from Row G to Row H]

The solution transferred to the row H can be used for DNA amplification by using a 5'-RACE method without any change.

Example 2 cDNA Synthesis Method from Sample Containing RNA Virus or Retrovirus

Adult human T-cell leukemia virus—Type 1 (HTLV-I) is a retrovirus having a single strand RNA as a genome. In order to detect a retrovirus secreted into cell supernatant by using the method of the present invention, ten thousands of cells (MT2) producing HTLV-I were cultured in a 24 well cell culture plate with 1 ml of PRMI-10% fetal bovine serum culture medium for 24 hours. First of all, DNase I was added to the cultured medium and treatment was conducted at 37° C. for 15 minutes to digest contaminated genomic DNA from cells. One μl of the solution was subjected to ten-fold serial dilution to obtain 10-fold dilution to 10 millions-fold dilution respectively with a cytolysis solution (100 mM Tris-HCl pH 7.5, 500 mM LiCl, 1% dodecyl lithium sulfate, 5 mM dithiothreitol), resulted in the preparation of seven kinds of diluted samples. One μl of each diluted sample was added to 2 μl of cytolysis solution (100 mM Tris-HCl pH 7.5, 500 mM LiCl, 1% dodecyl lithium sulfate, 5 mM dithiothreitol) in which Oligo-dT magnetic beads were suspended at the concentration of 10 mg/ml, and in a similar manner to Example 1, seven samples were subjected to steps through the reverse transcription reaction in the row E in parallel. A cytolysis solution containing no diluted sample was also subjected to the steps through the reverse transcription reaction in the row E as negative control in parallel with the seven samples.

In the row A, there was 3 μl in total of solution containing 100 mM Tris-HCl pH 7.5, 500 mM LiCl, 1% dodecyl lithium sulfate and 5 mM dithiothreitol.

In the row B, there was 3 μl in total of solution containing 10 mM Tris-HCl pH 7.5, 0.15M LiCl and 0.1% dodecyl lithium sulfate.

In the row C, there was 3 μl in total of solution containing 50 mM Tris-HCl pH8.3, 75 mM KCl, 3 mM $MgCl_2$, 0.1% Triton X-100, 0.5 mM dNTP, 5 mM DTT and 2 units of RNase inhibitor.

In the row D, there was 3 μl in total of solution containing 50 mM Tris-HCl pH8.3, 75 mM KCl, 3 mM $MgCl_2$, 0.1% Triton X-100, 0.5 mM dNTP, 5 mM DTT, 2 units of RNase inhibitor and 8 units of SuperScript III Reverse transcriptase.

In the row E, there was 3 μl in total of solution containing 10 mM Tris-HCl pH 7.5, 0.1% Triton X-100, 0.1 mM EDTA.

Figure 6:
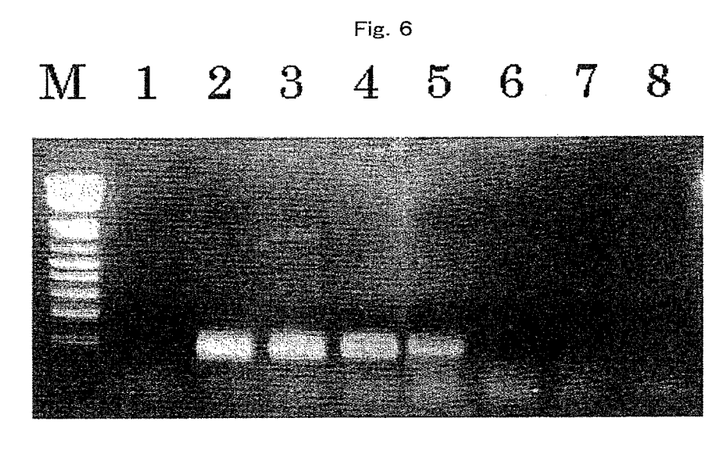
FIG. 6 shows the electrophoresis photograph obtained in Example 2; M: DNA size marker, 1: negative control, 2: ten-fold dilution, 3: hundred-hold dilution, 4: thousand-hold dilution, 5: ten thousand-hold dilution, 6: one hundred thousand-hold dilution, 7: one million-hold dilution, and 8: ten million-hold dilution).

One μl separated from the droplet in the row E was subject to the detection of HTLV-I virus present in the cell cultured medium by using a PCR method. In the PCR method PrimeSTAR® heat resistant DNA polymerase (Takara Bio Inc. Japan) and primers: 5'-gaggacggcttgacaaacatgggg-3' (SEQ ID NO: 1) and 5'-acagaagtctgagaaggtcagggc-3' (SEQ ID NO: 2) were used, and 40 cycles of reaction, which reaction consists of at 94° C. for 20 seconds, at 60° C. for 20 seconds and at 72° C. for 20 seconds, were performed. The PCR products were analyzed by means of an electrophoresis method using 2% agarose gel (referring to FIG. 6). In the samples of from 10-fold dilution to 10000-fold dilution of the cell cultured medium, the specific amplification derived from HTLV-I genome was observed.

Example 3

Transfer of Magnetic Beads from the Droplet Containing Bovine Serum Albumin

Figure 7:
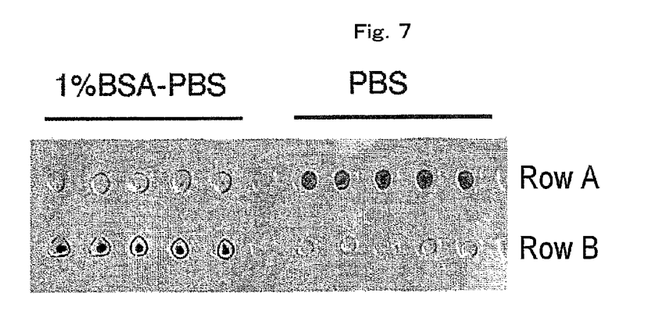
FIG. 7 shows the photograph of the reaction device obtained in Example 3.

In the row A, 3 μl of PBS (10 mM phosphate buffer, 120 mM NaCl, 2.7 mK KCl, pH 7.6) containing 25 μg of magnetic beads (Dynabeads®, 2.8 μm of the diameter) or 3 μl of 1% bovine serum albumin-PBS containing 25 μg of magnetic beads (Dynabeads®, 2.8 μm of the diameter) were spotted. In the row B, 1% bovine serum albumin-PBS were spotted. This was heated at 37° C. for 30 minutes by the means of the reaction device shown in FIG. 2 so that water vapor produced by the heating was precipitated on the substrate surface and thereby the production of micro droplets was accelerated. The room temperature was 20° C. Then, it stood at room temperature for 5 minutes, followed by that magnetic beads in the droplets in the row A were tried to be transferred in the row B by means of a small sized magnet. The photograph of the reaction device after the transfer is shown in FIG. 7. The results shows that the transfer of magnetic beads were observed in the droplets containing bovine serum albumin, but no transfer of magnetic beads was observed in the droplets without bovine serum albumin.

INDUSTRIAL APPLICABILITY

The present invention can be applied to large-scaled microamount continuous reactions for nucleic acids, proteins, lipids, sugars, complex carbohydrates and chemical compounds, as well as to immunostaining for immobilized cell(s) in the range of one to several dozen cells.

The invention claimed is:

1. A reaction device comprising a plurality of U-shaped projecting barriers arranged in a line on a surface of a substrate,
   wherein each U-shaped projecting barrier has two cutout portions, wherein openings formed by the two cutout portions have different sizes from each other,
   wherein each U-shaped projecting barrier substantially surrounds a space capable of holding a droplet, the space having a bottom defined by a first bottom surface,
   wherein the two cutout portions form a gap dividing each U-shaped projecting barrier, the gap having a bottom defined by a second bottom surface,
   wherein the first bottom surface, the second bottom surface, and a remainder of the surface of the substrate, other than the first bottom surface and the second bottom surface, are substantially level with each other,
   wherein at least the first bottom surface has pure water contact angle of 90 to 150 degrees; and
   wherein the reaction device is used in such a way that the surface having the plurality of U-shaped projecting barriers is downward.

2. The reaction device of claim 1, wherein at least a part of or all of said plurality of U-shaped projecting barriers are arranged in a matrix in a plane.

3. The reaction device of claim 1, wherein said space for holding a droplet of each U-shaped projecting barrier can hold a droplet of 0.5 µl to 200 µl.

4. The reaction device of claim 1, wherein the distance between the openings of said cutout portions is 0.5 to 10 mm.

5. The reaction device of claim 1, wherein said surface of the substrate comprises a resin selected from the group consisting of a paraffin resin, a polytetrafluoroethylene resin and a silicone resin.

6. The reaction device of claim 1, wherein said substrate comprises a coating made of a resin selected from the group consisting of a paraffin resin, a polytetrafluoroethylene resin and a silicone resin.

7. The reaction device of claim 1, wherein each space for holding a droplet defined by each U-shaped projecting barrier holds a droplet of an identical or different solution so that said solution does not contact another droplet held in the space for holding a droplet defined by another U-shaped projecting barrier.

8. The reaction device of claim 1, wherein spaces for holding a droplet defined by the U-shaped projecting barriers residing in the same row crosswise hold droplets of the same kind of solution.

9. The reaction device of claim 7, wherein said solution is a reaction solution or a washing solution, which solution contains a surface tension reducing agent.

10. The reaction device of claim 1, further comprising a housing member covering the surface having said U-shaped projecting barriers and a moisturizing member providing humidity in the space covered by said housing member.

11. A reaction method employing the reaction device of claim 1, comprising sequentially transferring a substance immobilized on magnetic beads in or between droplets containing a surface tension reducing agent held in the spaces for holding a droplet defined by said projecting barriers by means of a magnet on the opposite surface of the substrate to the surface having the projecting barriers, so that a reaction and/or a washing is performed.

12. A method of synthesizing cDNA employing the reaction device of claim 1 in which said device has at least two projecting barriers in one lengthwise row, comprising steps of:

(a) holding a droplet of cytolysis solution and a droplet of cDNA synthesis solution in the spaces for holding a droplet defined by said two projecting barriers, which both solutions contain a surface tension reducing agent, in this sequence, respectively;

(b) sequentially transferring mRNA immobilized on magnetic beads into the droplets held in the spaces for holding a droplet defined by said two projecting barriers by means of a magnet on the opposite surface of the substrate to the surface having the projecting barriers; and (c) obtaining cDNA immobilized on the magnetic beads.

13. The method of claim 12, wherein the reaction device having at least two projecting barriers in a plurality of longitudinal rows is used, the solutions held in the spaces for holding a droplet defined by the projecting barriers in each crosswise row are the same solution, mRNA immobilized on the magnetic beads moving on the longitudinal rows are different each other, and plural different kinds of cDNA are obtained as cDNA immobilized on the magnetic beads.

14. The method of claim 12, wherein said reaction device has at least four projecting barriers in one longitudinal row, the spaces for holding a droplet defined by said four projecting barriers hold a cytolysis solution, a mRNA washing solution, a cDNA synthesis solution and a cDNA washing solution in this sequence, respectively, and mRNA immobilized on the magnetic beads is sequentially transferred into the solutions held in the spaces for holding a droplet defined by said four projecting barriers.

15. The reaction device of claim 1, wherein each U-shaped projecting barrier is directly connected to and extends from the first bottom surface.

* * * * *